US007179613B2

(12) United States Patent
Rizzo et al.

(10) Patent No.: US 7,179,613 B2
(45) Date of Patent: Feb. 20, 2007

(54) METHODS OF SCREENING FOR A CANDIDATE MODULATOR OF GLUCOKINASE

(75) Inventors: Mark A. Rizzo, Nashville, TN (US); David W. Piston, Nashville, TN (US)

(73) Assignee: Vanderbilt University, Nashville, TN (US)

(*) Notice: Subject to any disclaimer, the term of this patent is extended or adjusted under 35 U.S.C. 154(b) by 249 days.

(21) Appl. No.: 10/838,167

(22) Filed: May 3, 2004

(65) Prior Publication Data

US 2005/0009129 A1   Jan. 13, 2005

Related U.S. Application Data

(60) Provisional application No. 60/467,885, filed on May 5, 2003.

(51) Int. Cl.
C12Q 1/48 (2006.01)
(52) U.S. Cl. .................................................. 435/15
(58) Field of Classification Search .................. 435/15
See application file for complete search history.

(56) References Cited

OTHER PUBLICATIONS

Aspinwall et al., "Roles of insulin receptor substrate-1, phosphatidylinositol 3-kinase, and release of intracellular $Ca^{2+}$ stores in insulin-stimulated insulin secretion in β-cells," *J. Biol. Chem.*, 275:22331-22338, 2000.
Bali et al., "Animal model for maturity-onset diabetes of the young generated by disruption of the mouse glucokinase gene," *J. Biol. Chem.*, 270(37):21464-21467, 1995.
Bell et al., "Glucoinase mutations, insulin secretion, and diabetes mellitus," *Annu. Rev. Physiol.*, 58:171-186, 1996.
Bell et al., "Gene for non-insulin-dependent diabetes mellitus (maturity-onset diabetes of the young subtype) is linked to DNA polymorphism on human chromosome 20q," *Proc. Natl. Acad. Sci., USA*, 88:1484-1488, 1991.
Brenman et al., "Interaction of nitric oxide synthase with the postsynaptic density protein PSD-95 and α1-syntrophin mediated by PDZ domains," *Cell*, 84:757-767, 1996.
Brocklehurst et al., "Stimulation of hepatocyte glucose metabolism by novel small molecule glucokinase activators," *Diabetes*, 53:535-541, 2004.
Chen et al., "Regulatory effects of glucose on the catalytic activity and cellular content of glucokinase in the pancreatic β cell," *J. Clin. Invest.*, 94:1616-1620, 1994.
Dukes et al., "Dependence on NADH produced during glycolysis for β-cell clucose signaling," *J. Biol. Chem.*, 269(15):10979-10982, 1994.
Efrat et al., "Ribozyme-mediated attenuation of pancreatic β-cell glucokinase expression in transgenic mice results in impaired glucose-induced insulin secretion," *Proc. Natl. Acad. Sci:, USA*, 91:2051-2055, 1994.
Erecinska et al., "Energy metabolism in islets of Langerhans," *Biochim. Biophys. Acta*, 1101(3):271-295, 1992.

Fajans, "Maturity-onset diabetes of the young (MODY)," *Diabetes/Metab. Rev.*, 5:579-606, 1989.
Fang et al., "Dextas1: a G protein specifically coupled to neuronal nitric oxide synthase via CAPON," *Neuron*, 28:183-193, 2000.
Froguel et al., "Familial hyperglycemia due to mutation sin glucokinase-definition of a subtype of diabetes mellitus," *N. Engl. J. Med.*, 328(10):697-702, 1993.
Froguel et al., "Close linkage of glucokinase locus on chromosome 7p to early-onset non-insulin-dependent diabetes mellitus," *Nature(London)*, 356:162-164, 1992.
Gerbitz et al., "Mitochondria and diabetes: genetic, biochemical and clinical implications of the cellular energy circuit," *Diabetes*, 45:113-126, 1996.
German, "Glucose sensing in pancreatic islet beta cells: the key role of glucokinase and the glycolytic intermediates," *Proc. Natl. Acad. Sci., USA*, 90:1781-1785, 1993.
Gidh-Jain et al., "Glucokinase mutations assiciated with non-insulin-dependent (type 2) diabetes mellitus have decreased enzymatic activity: implications for structure/function relationships," *Proc. Natl. Acad. Sci., USA*, 90:1932-1936, 1993.
Grimsby et al., "Allosteric activators of glucokinase: potential role in diabetes therapy," *Science*, 301:370-373, 2003.
Grupe et al., "Trasgenic knockouts reveal a critical requirement for pancreatic β cell glucokinase in maintainig glucose homeostasis," *Cell*, 83:69-78, 1995.
Hattersley et al., "Linkage of type 2 diabetes to the glucokinase gene," *Lancet*, 339(8805):1307-1310, 1992.
Heimberg et al., "Heterogeneity in glucose sensitivity among pancreatic β-cells is correlated to differences in glucose phosphorylation rather than transport," *EMBO J.*, 12(7):2873-2879, 1993.
Iynedjian, "Mammalian glucokinase and its gene," *Biochem. J.*, 293:1-13, 1993.
Jaffrey et al., "Protein S-nitrosylation: a physiological signal for neuronal nitric oxide," *Nat. Cell Biol.*, 3:193-197, 2001.
Jetton and Magnuson, "Heterogeneous expression of glucokinase among pancreatic β cells," *Proc. Natl. Acad. Sci., USA*, 89:2619-2623, 1992.
Kamata et al., "Structural basis for allosteric regulation of the monomeric allosteric enzyme human glucokinase," *Structure*, 12:429-438, 2004.
Kaneko et al., "Dual effect of nitric oxide on cytosolic $Ca^{2+}$ concentration and insulin secretion in rat pancreatic β-cells," *Am. J. Physiol. Cell. Physiol.*, 10:1152, 2003.

(Continued)

*Primary Examiner*—Maryam Monshipouri
(74) *Attorney, Agent, or Firm*—Fulbright & Jaworski

(57) ABSTRACT

The present invention relates to providing novel therapeutics for treating diabetes other glycemic disorders. Such therapeutics involve the signaling pathways that contribute to regulation of glucose-stimulated insulin secretion. Of particular interest are modulators of a key component in the glucokinase pathway. Thus, the present provides methods of screening for modulators of glucokinase activity, expression, translocation, conformation, nitrosylation and interaction with other molecules as useful target for pharmacological manipulation in the treatment of diabetes and other glycemic disorders.

12 Claims, 6 Drawing Sheets

OTHER PUBLICATIONS

Lachaal and Jung, "Interaction of facilitative glucose transporter with glucokinase and its modulation by ADP and glucose-6-phosphate," *J. Cellular Physiology*, 156:326-332, 1993.

Lajoix et al., "A neuronal isoform of nitric oxide synthase expressed in pancreatic β-cells contros insulin secretion," *Diabetes*, 50:1311-1323, 2001.

Leibiger et al., "Selective insulin signaling through A and B insulin receptors regulates transcription of insulin and glucokinase genes in pancreatic β cells," *Mol. Cell*, 7:559-570, 2001.

Liang et al., "Effects of alternate RNA splicing on glucokinase isoform activities in the pancreatic islet, liver, and pituitary," *J. Biol. Chem.*, 266(11):6999-7007, 1991.

Liang et al., "Glucose regulates glucokinase activity in cultured islets from rat pancreas," *J. Biol. Chem.*, 265(28):16863-16866, 1990.

Longo et al., "Oscillations in cytosolic free Ca2+, oxygen consumption, and insulin secretion in glucose-stimulated rat pancreatic islets," *J. Biol. Chem.*, 266(14):9314-9319, 1991.

Magnuson and Shelton, "An alternate promoter in the glucokinase gene is active in the pancreatic β cell," *J. Biol. Chem.*, 264(27):15936-15942, 1989.

Magnuson, "Glucokinase gene structure: functional implications of molecular genetic studies," *Diabetes*, 39:523-527, 1990.

Magnuson et al., "Rat glucokinase gene: structure and regulation by insulin," *Proc. Natl. Acad. Sci., USA*, 86(13):4838-4842, 1989.

Malaisse-Lagae and Mallaisse, "Hexose metabolism in pancreatic islets: regulation of mitochondrial hexokinase binding," *Biochem. Med. Metab. Biol.*, 39:80-89, 1988.

Malaisse, "Glucose-sensing by the pancreatic β-cell: the mitochondrial part," *Int. J. Biochem.*, 24(5):693-701, 1992.

Massa et al., "Interaction of 6-phosphofructo-2-kinase/fructose-2,6-biophosphatease (PFK-2/FBPase-2) with glucokinasae activates glucose phosphorylation and glucose metabolism in insulin-producing cells," *Diabetes*, 53:1020-1029, 2004.

Matschinsky et al., "Pancreatic β-cell glucokinase: closing the gap between theoretical concepts and experimental realities," *Diabetes*, 47:307-315, 1998.

Matschinsky, "Glucokinase as glucose sensor and metabolic signal generator in pancreatic β-cells and hepatocytes," *Diabetes*, 39:647-652, 1990.

Matschinsky, "Regulation of pancreatic β-cell glucokinase: from basics to therapeutics," *Diabetes*, 51:S394-404, 2002.

Meglasson and Matschinsky, "Pancreatic islet glucose metabolism and regulation of insulin secretion," *Diabetes Metab. Rev.*, 2:163-214, 1986.

Müller et al., "Porin proteins in mitochondria from rat pancreatic islet cells and white adipocytes; identification and regulation of hexokinase binding by the sulfonylurea glimepiride," *Arch. Biochem. Biophys.*, 308(1):8-23, 1994.

Nedvetsky et al., "There's NO binding like NOS binding: protein—protein interactions in NO/cGMP signaling," *Proc. Natl. Acad. Sci., USA*, 99:16510-16512, 2002.

Newgard and McGarry, "Metabolic coupling factors in pancreatic β-cell signal transduction," *Annu. Rev. Biochem.*, 64:689-719, 1995.

O'Rahilly et al., "Linkage analysis of the human insulin receptor gene in type 2 (non-insulin-dependent) diabetic families and a family with maturity onset diabetes of the young," *Diabetologia*, 31:407-414, 1988.

Postic et al., "Dual roles for glucokinase in glucose homeostasis as determined by liver and pancreatic β cell-specific gene knock-outs using Cre recombinase," *J. Biol. Chem.*, 274(1):305-315, 1999.

Rizzo et al., "A functional ling between glucokinase binding to insulin granules and conformational alterations in response to glucose and insulin," *J. Biol. Chem.*, 277(37):34168-34175, 2002.

Rotter et al., "Genetics of diabetes mellitus," In: *Diabetes Mellitus: Theory and Practice*, Rifkin and Porte (eds.), NY, 378-413, 1990.

Sener et al., "Hexose metabolisn in pancreatic islets: compartmetation of hexokinae in islet cells," *Arch. Biochem. Biophys.*, 251:61-67, 1986.

Shiraishi et al., "A novel glucokinase regulator in pancreatic β cells," *J. Biol. Chem.*, 276(4):2325-2328, 2001.

Smukler et al., "Exogenous nitric oxide and endogenous glucose-stimulated β-cell nitric oxide augment insulin release," *Diabetes*, 51:345-3460, 2002.

Stamler et al., "(S)NO signals: translocation, regulation, and a consensus motif," *Neuron*, 18:691-696, 1997.

Stubbs et al., "Subcellular localization, mobility, and kinetic activity of glucokinase in glucose-responsice insulin-secreting cells," *Diabetes*, 49:2048-2055, 2000.

Sweet et al., "Effect of a glucokinase inhibitor on energy production and insulin release in pancreatic islets," *Am. J. Physiol.*, 271:E606-E6265, 1996.

Tiedge et al., "Importance of cytsteine residues for the stability and catalytic activity of human pancreatic beta cell glucokinase," *Arch. Biochim. Biophys.*, 375(2):251-260, 2000.

Tiedge et al., "Modulation of human glucokinae intrinsic activity by SH reagents mirrors post-translational regulation of enzyme activity," *Biochim. Biophys. Acta*, 1337:175-190,1997.

Toyoda et al., "Glucokinase is concentrated in insulin-secretory granules of pancreatic β-cells," *Histochem. Cell. Biol.*, 112:35-40, 1999.

Wang and Iynedjian, "Modulation of glucose responsiveness of insulinoma β-cells by graded overexpression of glucokinase," *Proc. Natl. Acad. Sci., USA*, 94:4372-4377, 1997.

Watkins et al., "Imaging secretory vesicles by fluorescent protein insertion in propeptide than mature secreted peptide," *Traffic*, 3:461-471, 2002.

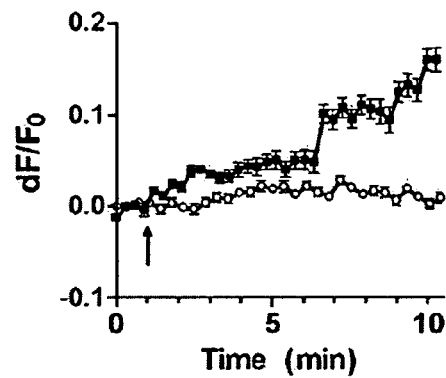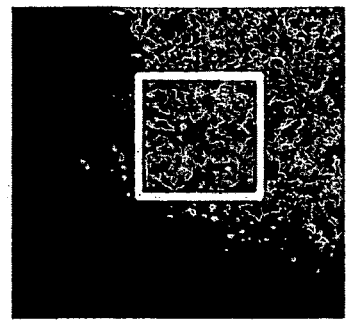
FIG. 1A
FIG. 1B
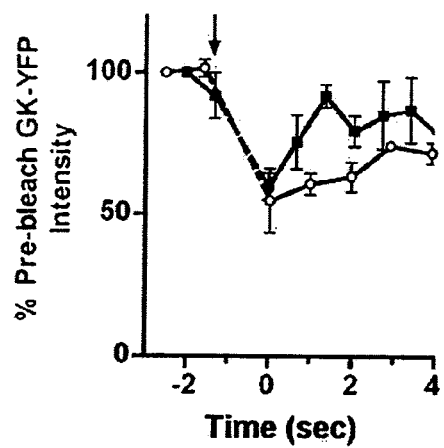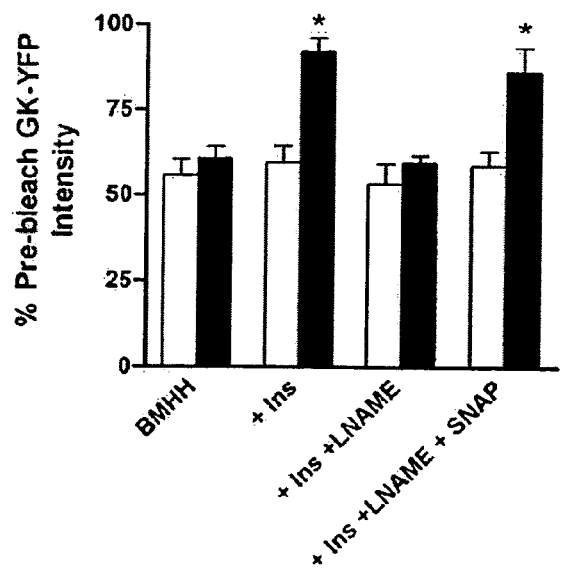
FIG. 1C
FIG. 1D

METHODS OF SCREENING FOR A CANDIDATE MODULATOR OF GLUCOKINASE

The present application claims the benefit of the filing date of U.S. Provisional Patent Application Ser. No. 60/467,885, filed on May 5, 2003. The entire text of the above-referenced disclosure is specifically incorporated herein by reference without disclaimer.

The government owns rights in the present invention pursuant to grant number DK60275, DK53434 and CA86283 from the National Institutes of Health.

BACKGROUND OF THE INVENTION

1. Field of the Invention

The present invention relates generally to the field of diabetes and other glycemic disorders. More particularly, it concerns methods of screening for modulators of glucokinase.

2. Description of Related Art

Non-insulin-dependent diabetes mellitus (NIDDM) is a major public health problem that affects 5–7% of the world population. Although most forms of NIDDM do not exhibit simple Mendelian inheritance, the contribution of heredity to the development of NIDDM has been recognized for many years (Cambridge, 1928; O'Rahilly et al., 1988; Fajans, 1989; Rotter et al., 1990). Early-onset NIDDM or maturity-onset diabetes of the young (MODY) shares many features with the more common form(s) of NIDDM whose onset occurs in midlife (Rotter et al., 1990). In addition, its early age of onset, clear mode of inheritance (autosomal dominant), high penetrance, and the availability of multi-generational pedigrees make MODY an attractive paradigm for genetic studies of NIDDM. Genetic studies have shown tight linkage of early-onset NIDDM and DNA markers on chromosome 20 (Bell et al., 1991) and the glucokinase gene (GCK) on chromosome 7 (Froguel et al., 1992)

At least three distinct mutations have been identified in MODY families (Bell et al., 1996). MODY 2 is characterized by mutations of the glucokinase gene, resulting in a predicted 50–100% decrease in glucokinase activity and impaired insulin secretion (Froguel et al., 1993; Hattersley et al., 1992). The occurrence of diabetes in heterozygous individuals who have some residual glucokinase activity underscores the role of glucokinase as the rate limiting glucose sensor of the beta cell.

Insulin-dependent diabetes mellitus (IDDM), or type 1 diabetes, is a T cell-mediated autoimmune disease. Although, a β-cell lesion is mediated by β-cell specific autoreactive T cells, environmental factors, notably a pancreatotropic virus, may also have an etiological role in this disease. Prevention of diabetes, but not the cure thereof, has been obtained with agents such as insulin, glutamic acid decarboxylase, and hsp60.

The importance of glucokinase (GK) in glucose hemostasis has been demonstrated by the association of GK mutants with diabetes mellitus in humans and by alteration in glucose metabolism in transgenic and gene knockout mice (Froguel et al., 1993; Gidh-Jain et al., 1993; Bali et al., 1995; Hariharan et al., 1997; Postic et al., 1999). Glucokinase (GK) activity is a major determinant of β-cell glucose metabolism and insulin secretion (Sweet et al., 1996; Matschinsky et al., 1998; Matschinsky, 2002). Thus, a complete model of its regulation is central to the understanding of glucose homeostasis and the pathogenesis of diabetic disease states.

To maintain physiological glucose-responsiveness, GK activity needs to be constrained within a very narrow range (Matschinsky et al., 1998; Wang and Iynedjian, 1997). Regulation of GK expression in beta cells has been widely studied and is induced mainly by glucose although it can be modulated by other factors, including insulin (Matschinsky, 2002; Leibiger et al., 2001). Post-translational regulation of GK has only more recently been described, and the mechanisms involved in this mode of regulation are not well known. Recent studies have shown that low levels of glucose cause an association of GK with secretory granules (Toyoda et al., 1999; Stubbs et al., 2000; Rizzo et al., 2002), and that this association correlates with a decrease in GK activity (Rizzo et al., 2002). Prolonged exposure to high glucose (>20 min) causes dissociation of GK from the granule along with conformational changes associated with activation. Glucose-stimulated GK regulation is blocked by inhibitors of insulin secretion, and insulin by itself can rapidly (<2 min) induce similar changes to GK localization and activity (Rizzo et al., 2002). This suggests that minute-to-minute regulation of GK activity and localization occurs through receptor-mediated signaling, and not by interaction between glucose and GK.

The molecular mechanism of GK association with secretory granules and the processes that modulate this association are unknown. The mechanism of GK association with secretory granules have been addressed by examining the role of nitric oxide synthase in its regulation. Neuronal nitric oxide synthase (nNOS) is activated by a rise in intracellular calcium, which is a known response of β cells response to glucose or insulin stimulation (Aspinwall et al., 2000); and nNOS is also known to be localized on insulin secretory granules (Lajoix et al., 2001). Nitric oxide (NO) has also been shown to have a stimulatory affect on glucose stimulated insulin secretion from both cultured β cell lines and pancreatic islets (Smukler et al., 2002; Kaneko et al., 2003). GK is one potential target for regulation by NO, since GK contains several cysteines that have been shown to be critical for maintaining catalytic activity (Tiedge et al., 2000).

SUMMARY OF THE INVENTION

The present invention provides a method of screening a candidate substance for modulation of glucokinase (GK) comprising (a) providing an insulin-responsive cell expressing a GK molecule; (b) contacting the cell with the candidate substance; and (c) measuring translocation of GK into the cytoplasm of the cell, wherein a change in the translocation of GK into the cytoplasm of the cell, as compared to that seen in a similar cell not treated with the candidate substance, indicates that the candidate substance is a modulator of GK.

In particular embodiments, the present invention contemplates the use of insulin-responsive cells such as an immortalized pancreatic cell, or an insulinoma cell. Such insulin-responsive cells may be treated with insulin, NO or high glucose concentrations. In some embodiments the insulin-responsive cell may be subjected to low glucose concentrations.

In further embodiments of the invention, translocation of GK into the cytoplasm of the cell may be measured by fluorescence photobleaching. In still another embodiment, the GK may be labeled with proteins such as a yellow fluorescent protein, and the secretory granules may be labeled with a cyan fluorescent protein.

In some aspects, the invention may further comprising performing a control reaction using an inhibitor of nitric oxide synthase.

The candidate substance as described herein, may be an organo-pharmaceutical, a peptide or protein, a nucleic acid, or an activator or inhibitor of GK.

In still another particular embodiment, the present invention provides a method of screening a candidate substance for modulation of glucokinase (GK) comprising (a) providing an insulin-responsive cell expressing a labeled GK molecule; (b) contacting the cell with the candidate substance; and (c) measuring the change in GK conformation, wherein a change in GK conformation, as compared to a similar GK molecule not treated with the candidate substance, indicates that the candidate substance is a modulator of GK.

In further embodiments of the invention, a change in GK conformation in a cell may be measured by FRET. In still another embodiment, the GK may be labeled on opposite ends with proteins such as a yellow fluorescent protein or a cyan fluorescent protein.

In still another particular embodiment, the present invention provides a method of screening a candidate substance for modulation of glucokinase (GK) comprising (a) providing an insulin-responsive cell expressing a GK molecule; (b) contacting the cell with (i) the candidate substance and (ii) insulin, NO or high glucose concentrations; (c) measuring the change in GK nitrosylation, wherein a change in GK nitrosylation, as compared to that seen in a similar cell not treated with the candidate substance, indicates that the candidate substance is a modulator of GK.

It is contemplated that the change in GK nitrosylation may be measured by biotin modification of nitrosylated proteins, followed by neutravidin separation.

In still a further particular embodiment, the present invention provides a method of screening a candidate substance for modulation of glucokinase (GK) comprising (a) providing an insulin-responsive cell expressing a labeled GK molecule and a labeled nNOS molecule; (b) contacting the cell with the candidate substance; and (c) measuring the change in the interaction of GK with nNOS, wherein a change in GK-nNOS interaction, as compared to that seen in a similar cell not treated with the candidate substance, indicates that the candidate substance is a modulator of GK.

In further embodiments of the invention, the interaction of GK with neuronal nitric oxide synthase (nNOS) in a cell may be measured by FRET. In still another embodiment, the GK may be labeled with proteins such as a yellow fluorescent and the nNOS labeled with a cyan fluorescent protein.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A–1E. Regulation of GK by insulin requires NO. FIG. 1A—βTC3 cells were starved for 4 h prior to loading with DAF-FM and analysis using confocal microscopy. The change in DAF intensity is represented as the change in fluorescence/initial fluorescence ($dF/F_0$) from the average of at least 10 cells treated with 100 nM insulin (indicated by the arrow, ■) or left untreated (○). FIG. 1B—FRAP measurements were taken in cells expressing GK-YFP and proinsulin-CFP by selectively photobleaching YFP fluorescence in a small region of the cell containing several granules. Fluorescence recovery of GK-YFP to CFP labeled insulin granules was measured after photobleaching GK-YFP in starved cells (○) and after insulin treatment (100 nM, 5 min, ■). The bleaching period is indicated by the arrow and broken lines. FIG. 1C—FRAP measurements show fluorescence intensity of granule-associated GK-YFP immediately following photobleaching (white bars) and 2 s after photobleaching (black bars) and expressed as % of pre-bleached fluorescent intensity. Cells were previously starved in BMHH for 3 h prior to insulin treatment (5 min), pretreatment with L-NAME (5 mM, 10 min) prior to insulin treatment (100 nM, 5 min), and after treatment with SNAP (100 μM, 1 min). Statistical significance from initial post-bleach intensity ($p<0.05$, t-test) is denoted by *. FIG. 1D—Cells expressing CFP-GK-YFP were examined for FRET by fluorescence microscopy as indicated. Statistical significance ($p<0.05$ by ANOVA or t-test as appropriate) is denoted by *. Cells were treated under the same conditions as in FIG. 1C. FIG. 1E—Nitrosylated proteins were precipitated with neutravidin-agarose after biotinylation of S-nitrosylated proteins from cell lysates. Cells were treated as above where indicated. GK was detected in unreacted lysates and precipitated fractions by Western blot using an antibody to GK (Jetton and Magnuson, 1992).

FIG. 2A—Mutant GK-YFP constructs were expressed in βTC3 cells. Nitrosylated proteins were biotinylated prior to immunoprecipitation of GK-YFP proteins and analysis by Western blot for GK (anti-GK) or biotinylated proteins using peroxidase-conjugated streptavidin (Strept-HRP). FIG. 2B—Association of the GK-YFP mutants with secretory granules was measured using FRAP in cells expressing the indicated GK-YFP construct and proinsulin-CFP. Fluorescence intensity of granule associated GK-YFP is expressed as % of prebleached intensity immediately after bleaching (white bars) and 2 s into recovery (black bars). Statistical significance from initial post-bleach intensity ($p<0.05$, t-test) is denoted by *. FIG. 2C—Mutations were made in CFP-GK-YFP and expressed in βTC3 cells. Cells were starved for 4 h in BMHH, and the normalized FRET ratio was calculated before (white bars) and after (black bars) stimulation with 100 nM insulin (5 min). Statistical significance from pretreatment FRET ratio ($p<0.05$, t-test) is denoted by*.

FIG. 3A—Endogenous GK, GK-YFP, and C371S GK-YFP were immunoprecipitated from cell lysates using anti-GK antibodies or anti-GFP antibodies for YFP-tagged proteins in combination with agarose-conjugated secondary antibodies. Precipitates were then heated to 37° C. for 10 min in the presence of 1 mM DEANO in PBS (lanes 3 and 4) or an equivalent volume of vehicle (DMSO) in PBS alone (lane 1 and 2). Pellets (1,3) and supernatants (2,4) were analyzed by SDS-PAGE and Western blot using anti-nNOS antibodies. (FIG. 3B) Cells expressing nNOS-CFP and GK-YFP or GK(C371S)-YFP were examined by two-photon microscopy before and after photobleaching with a 514 nm Ar laser (indicated by the hatched region). Average relative fluorescence (n=6) for cellular CFP (■) and YFP (□) intensities were plotted vs. time. A dotted line was drawn as a reference to indicate pre-bleach intensity. FIG. 3C—FRET between nNOS-CFP and either GK-YFP (●) or GK(C371S)-YFP (○) was examined in living cells by two-photon microscopy. FRET ratios were normalized to pre-treatment values (100%) prior to averaging (n=6) and plotted vs. time. Addition of insulin (100 nM) is indicated by the arrow. FIG. 3D—Cells were co-transfected with GK-YFP and nNOS-CFP-nuc and examined by confocal microscopy. In cells expressing both constructs, GK-YFP is found colocalized with nNOS in the nucleus (red arrows). GK-YFP did not localize to the nuclei of cells that were singly transfected with GK-YFP (white arrows). In the merged panel colocalization is indicated by red arrows.

DESCRIPTION OF ILLUSTRATIVE EMBODIMENTS

A. The Present Invention

Figure 1E:
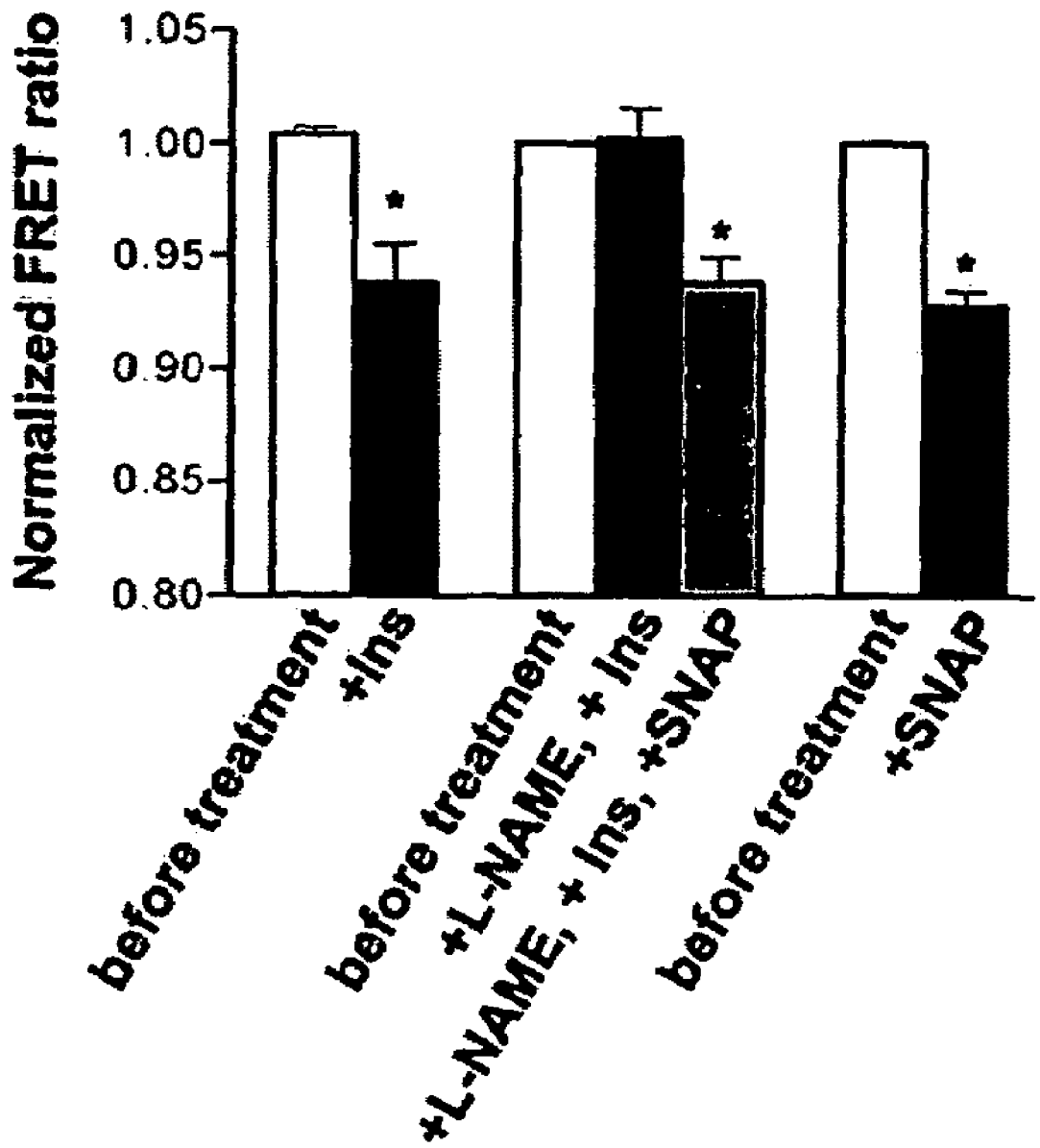

Glucokinase (GK) activity plays a key role in glucose-stimulated insulin secretion from pancreatic β cells. Insulin regulates GK activity by modulating its association with secretory granules, although little is known about the mechanisms involved in regulating this association. Using quantitative imaging of multi-color fluorescent proteins fused to GK, the inventors found that the dynamic association of GK with secretory granules is modulated through nitric oxide. Results in cultured β cells show that insulin stimulates NO production, and leads to S-nitrosylation of GK. Furthermore, inhibition of nitric oxide synthase (NOS) activity blocks insulin-stimulated changes in both GK association with secretory granules, and GK conformation. Mutation of cysteine 371 to serine blocks S-nitrosylation of GK and causes GK to remain tightly bound to secretory granules. In addition, GK was found to interact stably with neuronal nitric oxide synthase as detected by co-immuno-precipitation and fluorescence resonance energy transfer. Finally, attachment of a nuclear-localization signal sequence to NOS drives GK to the nucleus in addition to its normal cytoplasmic and granule targeting. These data show that the regulation of GK localization and activity in pancreatic β cells is directly related to nitric oxide production, and that the association of GK with secretory granules occurs through its interaction with NOS.

B. Glucokinase

Glucokinase (ATP:D-hexose 6-phosphotransferase; hexokinase IV) is expressed only in liver and pancreatic islets of Langerhans (β-cells) where distinct isoforms are generated due to tissue-specific alternate RNA splicing of the GK gene product. The glucokinase (GK) gene is 15.5-kilobases long, appears to be present as a single copy, and contains 10 exons that range in size from 96 to 977 base pairs. The transcription start site is located 127 nucleotides upstream from the translation initiation codon. Its 5' flanking DNA contains several regions similar to defined promoter elements. These include a probable "TATA box," an Sp1 binding site, and several elements related to liver-specific gene expression. It has been demonstrated that transcription of the glucokinase gene increased at least 20-fold when diabetic rats were treated with insulin for 2 hr (Magnuson et al., 1989).

In β-cells GK plays a key role in the regulation of insulin secretion and glucose homeostasis (Magnuson, 1990; Matschinsky, 1990; Pilkis and Granner, 1992; Magnuson et al., 1989; Magnuson and Shelton, 1989). β-cells, a neuroendocrine islet cell population, secrete insulin from ultrastructurally distinct secretory granules. In the hepatocyte, the phosphorylation of glucose by glucokinase facilitates the uptake and metabolism of glucose by maintaining a gradient for glucose transport into these cells thereby regulating hepatic glucose disposal.

Glucokinase catalyzes the conversion of glucose to glucose 6-phosphate, the rate-limiting step in glucose utilization by pancreatic β-cells, thus translating fluctuations in intracellular glucose levels to changes in the rate of glycolysis. Unlike the other mammalian hexokinases, which all have high affinity for glucose, the Km of glucokinase is in the millimolar range. Consequently, glycolytic flux becomes proportional to the extracellular glucose concentration in glucokinase-expressing cells as long as glucose uptake is not rate-limiting for its further metabolism (Matschinsky, 1996; Iynedjian, 1993). Furthermore, the enzyme is not sensitive to feedback inhibition by glucose 6-phosphate (G6P), allowing the liver to sustain high metabolic flux despite elevated intracellular concentration of G6P. Glucokinase gene expression level in β-cells is correlated to cellular glucose sensitivity both in vivo (Efrat et al., 1994; Grupe et al., 1995) and in vitro (Heimberg et al., 1993), suggesting that the enzyme is a constituent of the β-cell glucose sensor. Increases in the rate of glucose usage by β-cells, mediated by GK, are followed by changes in $K^+$ and $Ca^{2+}$ channel conductance, a resultant increase in intracellular $[Ca^{2+}]$, and then an increase in the rate of insulin secretion.

C. Glucokinase Mechanism

Glucokinase is bound to the outer surface of the mitochondria in β-cells through its interaction with the mitochondrial membrane protein porin (also called VDAC or voltage-dependent anion channel) (Malaisse-Lagae and Malaisse, 1988; Sener et al., 1986; Muller et al., 1994). This situation is analogous to the interaction of hexokinase II with mitochondria in liver and skeletal muscle, and hexokinase I with mitochondria in liver (Gerbitz et al., 1996; Weiler et al., 1985; Adams et al., 1988). Because porin is associated with the mitochondrial adenine nucleotide translocator (ANT), binding of GK to the pore may facilitate delivery of oxidatively produced ATP to the enzyme, which preferentially uses ATP produced by the mitochondria (Rasschaert and Malaisse, 1990). Delivery of ADP back to the mitochondria for resynthesis of ATP by complex V may also be a function of this association (Laterveer et al., 1994).

Following glucose phosphorylation, the subsequent fate of G6P is almost entirely via metabolism through the glycolytic pathway, because the pentose phosphate shunt is relatively inactive in pancreatic β-cells (Ashcroft et al., 1972), and glycogen synthesis accounts for no more than 7% of glucose flux (Meglasson and Matschinsky, 1986). The glycolytic pathway distal to G6P appears particularly important for insulin secretion with regards to the production of NADH (Dukes et al., 1994; MacDonald and Fahien, 1990), which is efficiently shuttled from the cytosol to the mitochondria. There, it enters the electron transport chain at complex I and fuels oxidative production of ATP. The next clear-cut correlation between cellular metabolism and insulin secretion is the rise in the intracellular ATP:ADP ratio (Erecinska et al., 1992; Longo et al., 1991; Ashcroft et al., 1973), which triggers closure of the ATP-sensitive $K^+$ channel at the β-cell plasma membrane, resulting in depolarization of the cell. The increase in ATP:ADP following a glucose load is believed to be due to a rise in ATP of predominantly oxidative origin (Malaisse, 1992). Using a series of glycolytic inhibitors, Dukes et al. (1994) have demonstrated that only oxidatively derived ATP could trigger closure of the $K^+$ channel in β-cells. This membrane depolarization leads to opening of $Ca^{2+}$ channels with influx of calcium to the cytosol. It is the rise in intracellular calcium that ultimately causes the exocytosis of insulin.

Although the initial step in glucose-mediated insulin secretion is the uptake of glucose into the β-cells via glut 2 glucose transporters, this uptake significantly exceeds glucose utilization and is therefore not rate-limiting for the sequence of events that triggers insulin release (Matschinsky, 1996; Newgard and McGarry, 1995). Rather, it is the subsequent phosphorylation of glucose to glucose-6-phosphate (G6P) that defines the set point at which secretion is initiated. Pancreatic islets of Langerhans ("islets") contain both a low Km (hexokinase I) and a high Km (glucokinase=hexokinase IV) glucose phosphorylating activity. The Km of glucokinase is 6–11 mM, while that of hexokinase I is 10–100 mM. Furthermore, hexokinase I is inhibited by its product, G6P, while glucokinase is not. The majority of glucose phosphorylating activity in β-cells is accounted for by the high Km glucokinase. The low Km hexokinase I is believed to be inactive in the islets due to inhibition by G6P. As a result, insulin secretion normally occurs when the blood glucose begins to rise above the physiological level of 5.5 mM.

D. Screening for Modulators

1. Screening Methods for Glucokinase Modulators

The present invention comprises methods for identifying modulators of glucokinase activity or expression. Glucokinase may be used as a target in screening for compounds that inhibit, decrease, down-regulate or activate its expression or activity in cells, such as an insulin-responsive cell e.g., an immortalized pancreatic cells. These assays may comprise random screening of large libraries of candidate substances. Alternatively, the assays may be used to focus on particular classes of compounds selected with an eye towards structural attributes that are believed to make them more likely to modulate the function of glucokinase. By function, it is meant that one may assay for inhibition or activation of expression of glucokinase in insulin-responsive cells; a change in translocation of glucokinase into the cytoplasm; a change in glucokinase conformation; a change in glucokinase nitrosylation; or a change in glucokinase interaction with other molecules such as neuronal nitric oxide synthase (nNOS).

To identify a glucokinase modulator, one generally will determine glucokinase modulation in the presence and absence of the candidate substance, wherein a modulator is defined as any substance that regulates, reduces, inhibits, decreases, or activates glucokinase activity or expression. For example, a method may generally comprise:

a) providing a cell;
b) contacting the cell with a candidate substance; and
c) measuring translocation of glucokinase into the cytoplasm, wherein a change in the translocation of glucokinase into the cytoplasm of a cell, as compared to that seen in a similar cell not treated with the candidate substance, indicates that the candidate substance is a modulator of glucokinase.

Assays may be conducted in cell free systems, in isolated cells, or in organisms including transgenic animals. It will, of course, be understood that all the screening methods of the present invention are useful in themselves notwithstanding the fact that effective candidates may not be found. The invention provides methods for screening for such candidates, not solely methods of finding them.

a. Modulators

As used herein the term "candidate substance" or "candidate compound" refers to any molecule that may potentially inhibit or activate the expression or activity of glucokinase. A glucokinase modulator, may be a compound that overall affects translocation of glucokinase into the cytoplasm; glucokinase conformation; glucokinase nitrosylation; or glucokinase interaction with other molecules such as neuronal nitric oxide synthase (nNOS). Thus, such a modulator may further regulate glucokinase expression, translocation or transport, function, post-translational modification, location, or more directly by preventing or promoting its activity, such as by binding glucokinase. Any compound or molecule described in the methods and compositions herein may be an glucokinase modulator.

The candidate substance may be a protein or fragment thereof, a small molecule, or even a nucleic acid molecule. It may prove to be the case that the most useful pharmacological compounds will be compounds that are structurally related to glucokinase or that bind glucokinase. Using lead compounds to help develop improved compounds is known as "rational drug design" and includes not only comparisons with known modulators, but predictions relating to the structure of target molecules.

Candidate substances, compounds or modulators of the present invention will likely function to regulate i.e., inhibit, decrease, or activate the expression or activity of glucokinase in an insulin-responsive cell such as a pancreatic cell. Such candidate substances may be inhibitors, or activators of insulin. These candidate compounds may be antisense molecules, ribozymes, antibodies (including single chain antibodies), or organopharmaceuticals, but are not limited to such.

b. Rational Drug Design

The present invention also provides methods for developing drugs that modulate glucokinase activity or expression that may be used to treat diabetes. One such method involves the prediction of the three dimensional structure of a validated glucokinase modulator target using molecular modeling and computer stimulations. The resulting structure may then be used in docking studies to identify potential small molecule inhibitors that bind in the enzyme's active site with favorable binding energies. Modulators identified may then be tested in biochemical assays to further identify glucokinase drug targets for diabetes.

Rational drug design is therefore used to produce structural analogs of substrates for glucokinase. By creating such analogs, it is possible to fashion drugs which are more active or stable than the natural molecules, which have different susceptibility to alteration or which may affect the function of various other molecules. In one approach, one would generate a three-dimensional structure for the glucokinase targets of the invention or a fragment thereof. This could be accomplished by X-ray crystallography, computer modeling or by a combination of both approaches.

It also is possible to use antibodies to ascertain the structure of a target compound modulator. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen a large number of related (and unrelated) compounds for activity. Combinatorial approaches also lend themselves to rapid evolution of potential drugs by the creation of second, third and fourth generation compounds modeled from active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable compounds include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate modulators.

In addition to the inhibiting compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An modulator according to the present invention may be one which exerts its inhibitory or activating effect upstream, downstream or directly on glucokinase. Regardless of the type of modulator identified by the present screening methods, the effect of the inhibition or activation by such a compound results in the regulation in glucokinase activity or expression as compared to that observed in the absence of the added candidate substance.

The term "drug" is intended to refer to a chemical entity, whether in the solid, liquid, or gaseous phase which is capable of providing a desired therapeutic effect when administered to a subject. The term "drug" should be read to include synthetic compounds, natural products and macromolecular entities such as polypeptides, polynucleotides, or lipids and also small entities such as neurotransmitters, ligands, hormones or elemental compounds. The term "drug" is meant to refer to that compound whether it is in a crude mixture or purified and isolated.

2. Fluorescence Recovery After Photobleaching (FRAP) Assay

Fluorescence Recovery After Photobleaching (FRAP) is a technique used to assess the structure of artificial and biological membranes. FRAP has proved to be a popular means for observing and quantifying the movement of molecules, particularly due to diffusion. FRAP has being used to measure the lateral diffusion of various membrane or cytoplasmic constituents and to characterize the mobility of plasma membrane receptors and lipids under various conditions; e.g., during cell locomotion and hypoxic injury. FRAP has also been used to examine cytoskeletal dynamics and characterize sperm plasma membranes before and after capacitation.

In general, a specimen of interest is loaded with fluorescently tagged molecules and the fluorescence of a defined region of the specimen is bleached. The recovery of fluorescence in the bleached area depends on the mobility of the fluorescent molecules.

More particularly, the FRAP assay is based on the principal of observing the rate of recovery of fluorescence due to the movement of a fluorescent marker into an area of the membrane which contains this same marker but which has been rendered non-fluorescent via an intense photobleaching pulse of laser light. The two-dimensional diffusion coefficient (D) of the fluorophore is related to both its rate and extent of recovery. Before bleaching occurs, the distribution of fluorescence is recorded by a laser scanned confocal image using laser attenuation to reduce bleaching during image acquisition. A bleaching scan is performed with the laser attenuation reduced to the minimum and the scanning parameters changed with only a subregion of the specimen scanned and bleached. The laser attenuation and scan parameters are returned to the values used in the pre-bleach image and changes in the post-bleach distribution of fluorescence are recorded in a series of confocal images.

Thus, using the FRAP assay, the translocation of glucokinase into the cytoplasm of a cell can be measured as described herein.

The flourescent markers/dye used is not believed to be important, so long as it is capable of being expressed in the specimen of interest. Examples of fluorescent labels/marker/dyes are well known to one of skill in the art. Some examples of markers/dyes contemplated in the present invention include but are not limited to: 4-amino-5-methylamino-2',7'-difluorofluorescein diacetate (DAF-FM) (Kojima et al., 1999), an indicator dye whose fluorescence increases upon reaction with NO; FITC molecules; GFP; rhodamine, Cy3, or DsRed; Cy5 or TOTO-3; and DAPI or coumarin.

3. FRET Assay

To measure a change in glucokinase conformation due to regulation by agents such as nitric oxide production, the present invention employs the fluorescence resonance energy transfer (FRET) technique. This is a powerful technique for measuring molecular interactions at Ångstrom distances. This technique measures the distance-dependent interaction between the electronic excited states of two dye molecules in which excitation is transferred from a donor molecule to an acceptor molecule without emission of a photon. The efficiency of FRET is dependent on the inverse sixth power of the intermolecular separation, making it useful over distances comparable with the dimensions of biological macromolecules. Thus, FRET is an important technique for investigating a variety of biological phenomena that produce changes in molecular proximity. When FRET is used as a contrast mechanism, colocalization of proteins and other molecules can be imaged with spatial resolution beyond the limits of conventional optical microscopy. In other embodiments of the present invention, the use of the FRET assay is contemplated for measuring the change in interaction of glucokinase with a secondary agent such as neuronal nitric oxide synthase (nNOS).

Primary conditions that must be taken into consideration using the FERT assay include: (a) donor and acceptor molecules must be in close proximity (typically 10–100 Å); (b) the absorption spectrum of the acceptor must overlap the fluorescence emission spectrum of the donor; and (c) donor and acceptor transition dipole orientations must be approximately parallel.

This technique also employs the use of fluorescent proteins that may be fused in frame to the molecule of interest. Examples of such fluorescent proteins are the cyan fluorescent protein (CFP) or the yellow fluorescent protein (YFP), but are not limited to such.

4. Nitrosylation

The present invention contemplates measuring the change in glucokinase nitrosylation in a cell such as an insulin-responsive cell. Nitrosylation as is known to the skilled artisan refers to the addition of NO to a thiol group (SH), oxygen, carbon or nitrogen by chemical means. The source of NO may be endogenous NO or endothelium-derived relaxing factor, or other nitrosylating agents, such as nitroglycerin, nitroprusside, nitrosothiols, nitrous acid or any other related compound. In addition to thiol groups, proteins and amino acids possess other sites which can be nitrosylated. For example, such sites may include, but are not limited to, oxygen, nitrogen, and carbon.

In particular aspects of the present invention glucokinase nitrosylation may be measured by biotin modification of nitrosylated proteins followed by separation by binding to neutravidin agarose. Nitrosylation of proteins e.g., S-nitrosylation of proteins, may be detected by a three-step method, which converts nitrosylated cysteines into biotinylated cysteines. First, free thiols may be blocked by incubation with the thiol-specific methylthiolating agent methyl methanethiosulfonate (MMTS). Sodium dodecyl sulphate (SDS) may be used to ensure access of MMTS to buried cysteines. Ideally the conditions selected for use should prevent MMTS from reacting with nitrosothiols or pre-existing disulphide bonds. Second, after blocking of free thiols, nitrosothiol bonds may be decomposed with ascorbate, resulting in the reduction of nitrosothiols to thiols. Third, the newly formed thiols may then be reacted with N-[6-(biotinamido)hexyl]-3'-(2'-pyridyldithio) propionamide (biotin-HPDP), a sulphydryl-specific biotinylating reagent. The biotinylated proteins may then be separated by binding to neutravidin agarose. Protocols for biotinylation and isolation of nitrosylated proteins are described in Jaffrey et al. (2001).

5. In cyto Assays

The present invention also contemplates the screening of compounds for their ability to modulate glucokinase activity or expression in cells. Various cell lines can be utilized for such screening assays, including cells specifically engineered for this purpose. The present invention particularly contemplates the use of insulin-responsive cells e.g., immortalized pancreatic cells or insulinoma cells which express a high level of glucokinase and thus may provide an easier baseline for measurement. Depending on the assay, culture may be required. The cell is examined using any of a number of different physiologic assays. Alternatively, molecular analysis may be performed, for example, looking at protein expression, mRNA expression (including differential display of whole cell or polyA RNA) and others by methods as described herein and that are well known to those of skill in the art.

6. In vivo Assays

In vivo assays involve the use of various animal models, including transgenic animals that have been engineered to have specific defects such as glucokinase over expression, or that carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for inhibitors may be conducted using an animal model derived from any of these species.

In such assays, one or more candidate substances are administered to an animal, and the ability of the candidate substance(s) to alter one or more characteristics, as compared to a similar animal not treated with the candidate substance(s), identifies a modulator. The characteristics may be any of those discussed above with regard to glucokinase expression or function, or it may be broader in the sense of "treating" the condition present in the animal.

Treatment of these animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve measuring toxicity and dose response can be performed in animals in a more meaningful fashion than in in vitro or in cyto assays.

7. Transgenic Animals

The present invention also contemplates the use of transgenic animals to understand glycemic disorders/diseases and glucokinase function. A transgenic animal of the present invention may involve an animal in which Glucokinase or a Glucokinase modulator is expressed temporally or spatially in a manner different than a non-transgenic animal. Thus, it is contemplated that the transgene, such as a gene encoding Glucokinase or a Glucokinase modulator, may be expressed in a different tissue type or in a different amount or at a different time than the endogenously expressed version of the transgene.

In a general aspect, a transgenic animal is produced by the integration of a given transgene into the genome in a manner that permits the expression of the transgene, or by disrupting the wild-type gene, leading to a knockout of the wild-type gene. Methods for producing transgenic animals are generally described by Wagner and Hoppe (U.S. Pat. No. 4,873,191; which is incorporated herein by reference), Brinster et al. (1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

U.S. Pat. No. 5,639,457 is also incorporated herein by reference to supplement the present teaching regarding transgenic pig and rabbit production. U.S. Pat. Nos. 5,175,384; 5,175,385; 5,530,179, 5,625,125, 5,612,486 and 5,565,186 are also each incorporated herein by reference to similarly supplement the present teaching regarding transgenic mouse and rat production. Transgenic animals may be crossed with other transgenic animals or knockout animals to evaluate phenotype based on compound alterations in the genome.

E. Pharmaceutical Compositions and Routes of Administration

Pharmaceutical compositions of the present invention may comprise an effective amount of one or more modulator that inhibits or activates glucokinase expression or activity, and/or an additional agent, dissolved or dispersed in a pharmaceutically acceptable carrier to a subject. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one glucokinase modulator or additional active ingredient will be known to those of skill in the art in light of the present disclosure, and as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289–1329, incorporated herein by reference). Except insofar as any conventional carrier is incompatible with the active ingredient, its use in the therapeutic or pharmaceutical compositions is contemplated.

A pharmaceutical composition of the present invention may comprise different types of carriers depending on whether it is to be administered in solid, liquid or aerosol form, and whether it needs to be sterile for such routes of administration as injection. A pharmaceutical composition of the present invention can be administered intravenously, intradermally, intraarterially, intraperitoneally, intraarticularly, intrapleurally, intranasally, topically, intramuscularly, intraperitoneally, subcutaneously, subconjunctival, intravesicularlly, mucosally, intrapericardially, intraumbilically, orally, topically, locally, by inhalation (e.g., aerosol inhalation), by injection, by infusion, by continuous infusion, via a catheter, via a lavage, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The number of doses and the period of time over which the dose may be given may vary. The practitioner responsible for administration will, in any event, determine the concentration of active ingredient(s) in a composition and appropriate dose(s), as well as the length of time for administration for the individual subject.

In certain embodiments, pharmaceutical compositions may comprise, for example, at least about 0.1% of an active compound. In other embodiments, the active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

A glucokinase modulator(s) of the present invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In certain aspects of the invention, the glucokinase modulators are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations of any of the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

F. Combination Therapies with Glucokinase Modulator(s)

In order to increase the effectiveness of a diabetes treatment with the compositions of the present invention, such as a glucokinase modulator, it may be desirable to combine these compositions with other therapeutic agents. For example, the treatments/therapies for diabetes and/or glycemic disorders, for example insulin therapy, may be implemented with therapeutic agents of the present invention. Thus, in the present invention, it is contemplated that glucokinase modulator(s) may be used in conjunction with gene therapy, or insulin therapy or other biological intervention, in addition to insulin regulators.

This process may involve contacting the cell(s) with a glucokinase modulator and a therapeutic agent at the same time or within a period of time wherein separate administration of the modulator and an agent to a cell, tissue or organism produces a desired therapeutic benefit. The terms "contacted" and "exposed," when applied to a cell, tissue or organism, are used herein to describe the process by which a glucokinase modulator and/or therapeutic agent are delivered to a target cell, tissue or organism or are placed in direct juxtaposition with the target cell, tissue or organism. The cell, tissue or organism may be contacted (e.g., by administration) with a single composition or pharmacological formulation that includes both a glucokinase modulator and one or more agents, or by contacting the cell with two or more distinct compositions or formulations, wherein one composition includes a glucokinase modulator and the other includes one or more agents.

The glucokinase modulator may precede, be concurrent with and/or follow the other agent(s) by intervals ranging from minutes to weeks. In embodiments where the glucokinase modulator and other agent(s) are applied separately to a cell, tissue or organism, one would generally ensure that a significant period of time did not expire between the time of each delivery, such that the inhibitor and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the modulator. In other aspects, one or more agents may be administered within of from substantially simultaneously, about 1 minute, about 5 minutes, about 10 minutes, about 20 minutes about 30 minutes, about 45 minutes, about 60 minutes, about 2 hours, or more hours, or about 1 day or more days, or about 4 weeks or more weeks, or about 3 months or more months, or about one or more years, and any range derivable therein, prior to and/or after administering the glucokinase modulator.

Various combinations of a glucokinase modulator(s) and a second therapeutic may be employed in the present invention, where a glucokinase modulator is "A" and the secondary agent, such as an insulin therapy, glycemic therapeutic or any diabetes therapeutic agent is "B":

| | | | | | | |
|---|---|---|---|---|---|---|
| A/B/A | B/A/B | B/B/A | A/A/B | A/B/B | B/A/A | B/B/B/A |
| B/B/A/B | A/A/B/B | A/B/A/B | A/B/B/A | B/B/A/A | B/A/B/A | B/A/A/B |
| A/A/A/B | B/A/A/A | A/B/A/A | A/A/B/A | A/B/B/B | B/A/B/B | |

Administration of modulators to a cell, tissue or organism may follow general protocols for the administration of diabetic and glycemic therapeutics, taking into account the toxicity, if any. It is expected that the treatment cycles would be repeated as necessary. In particular embodiments, it is contemplated that various additional agents may be applied in any combination with the present invention. Suitable agents or therapeutics that have been used in treating diabetes and glycemic disorders include: 1) delay the onset of disorder by administration of depleting CD4 antibodies such as GK 1.5 and, to a lesser extent, CD8, CD44, CD45RA, or CD45RB antibodies; 2) targeting of T-cell homing molecules, aimed at diverting pathogenic T cells or their precursors from migrating to the islets using anti-VLA-1, anti-VLA-4, anti-CD43, and anti-L-selectin (CD62L) antibodies; 3) other molecules that may be employed include: anti-CD3, anti-CD 4, anti-CD8, anti-Thy 1.2, antilymphocyte globulin, VLA-4/Ig fusion protein, and anti-CD62L. Other therapuetic that may be used in combination with the modulator(s) of the present invention are as follows:

1. Chemical Immunosuppressants

Another therapy that may be used in combination with a glucokinase modulator of the present invention involve agents that reversibly block T-cell activation. At present, this is achieved using chemical immunosuppressants. Most drugs used in organ transplantation where T cells are also involved have been used, and these include, notably, cyclosporin A, azathioprine, rapamycin, FK506, and deoxyspergualin but are not limited to such. These drugs essentially worked when given early in the course of the disease as a preventive, but not a curative, treatment.

2. T-cell Receptors

T-cell-receptor(TCR)-mediated recognition of β-cell autoantigens is a central step in the diabetes pathogenesis, at both the triggering and the effector phases. Thus, blocking TCRs provides another strategy for treating diabetes. Such approaches may comprise the use of agents including, but not limited to: TCRαβ antibody, CD3 antibody, Vβ8 antibody. These agents and related compounds are contemplated in combination with a glucokinase modulator in treating diabetes and other glycemic disorders.

3. MHC Molecules

Peptides of β-cells are presented to T cells in the context of MHC molecules. Thus, administration of either class I or class-II specific antibodies may be provided in conjunction with a glucokinase modulator of the present invention for the treatment of diabetes and other glycemic disorders. Such molecules include but are not limited to anti-class-I, anti-class-II, Class I, I-A, I-E, antibodies.

4. Costimulation and Adhesion Molecules

The activation of autoreactive T cells specific to β-cells antigens involves a number of costimulation and adhesion molecules. Thus, the present invention contemplates the use of such costimulation and adhesion molecules in combination with a glucokinase modulator(s) of the present invention in treating diabetes and other glycemic disorders. Such costimulation and adhesion molecules include but are limited to: anti-CD28, CTLA-4-Ig fusion protein, anti-B7.2, anti-CD40L, anti-ICAM-1, soluble ICAM-1, anti-Mac, and anti-LFA-1.

5. Cytokine Blockade

A number of cytokines are know to be involved in the differentiation and activation of various T cell subsets which contribute to diabetes and other glycemic disorders. Antibodies directed at cytokines or cytokine receptors inhibiting the onset of diabetes relate to Th1 cells. Thus, it is contemplated that agents such as IFN-γ, anti-IFN-γ, IFN-γR/IgG1 fusion protein; IL-2, anti-IL-2R, IL-2R/Ig fusion protein, IL-2 diphtheria-toxin protein; IL-12, anti-IL-12, IL-12 antagonist (p40)2; IL-1 antibody, IL-1 antagonist; IFN-α; IL-6, and Lymphotoxin receptor may be used in combination with a glucokinase modulator(s) of the present invention.

6. Pharmacologically Active Cytokines

Many of the strategies resulting in stimulation of regulatory cells may also be involved in the suppressive effect of cytokines acting either systematically or locally at the islet level. Therefore, onset of diabetes may also be prevented by the direct administration of regulatory cytokines. Examples of such regulatory cytokines contemplated by the present invention in combination with a glucokinase modulator include, but are not limited to, IL-4, IL-10, IL-13, IL-3, G-CSF, Lymphotoxin, IL-11, IL-1α, and TNF-α.

7. Soluble β-cell Autoantigens

Prevention, but not the cure for diabetes has been obtained with insulin, glutamic acid decarboxylase (GAD) and hsp60. Insulin in combination with IL-10 has also been effective in preventing diabetes. Thus, the present invention contemplates the use of these agents in combination with a glucokinase modulator as a more effective therapeutic modality for treating diabetes and other glycemic disorders. Also contemplated are: anti-GAD antibody, P277 peptide, and pancreatic extracts.

8. Stimulation of Regulatory T cells

The diabetes autoimmune response is tightly controlled by a variety of regulatory T cells and involve their stimulation. Thus, the present invention contemplates the use of nondepleting anti-T-cell monoclonal antibodies, stimulation of innate immunity, pathogens, viruses and parasites which have been shown to prevent the onset of diabetes, in combination with the glucokinase modulator(s). Nondepleting anti-T-cell antibodies include anti-CD3, ant CD4 and superantigens. Stimuation of innate immunity may be accomplished by administering α-galactosylceramide. Pathogens include a variety of bacteria which have been shown to prevent the onset of diabetes such as, *Mycobacterium bovis*, *Mycobacterium avium*, Complete Freund's adjuvant, *Lactobacillus casei*, *Streptococcal* extract, *Klebsiella* extract, *Escherichia* coli in combination with oral insulin; viruses such as mouse hepatitis virus, lactate dehydrogenase virus, lymphocytic choriomeningitis virus; and parasites such as, filariae and schistosomes.

9. Gene Therapy

The present invention also contemplates gene therapy in conjunction with a glucokinase modulator. Immune-based gene therapy include β-cell antigens, IL-4, IL-4/IgG1 fusion protein, IL-10, ICAM-1, IFN-γR/IgG1 fusion protein, TGF-β, and calcitonin 10. Cell Therapy Cell therapy is also contemplated in combination with glucokinase modulator of the present invention in treating diabetes and other glycemic disorders. Such therapies include islet or segmental pancreas transplantation, intrathymic islet transplantation, allogenic or syngenic bone marrow transplantation, infusion of mononuclear cells such as dendritic cells, natural killer T cells, CD4 cell lines (anti-Ia$^{g7}$), and allogeneic cells such as macrophages and spleen cells.

11. Inhibition of β-Cell Lesion

Other agents involved in inhibiting the effector mechanism leading to destruction of β-cells may also be employed in combination with a glucokinase modulator of the present invention. Such agents may comprise nicotinamide; antioxidants which include vitamin E, probucol analog, probucol in combination with deflazacort and aminoguanidine; anti-inflammatory agents such as pentoxifylline and rolipram. Other agents may include nitric oxide inhibitors, anti-TCR antibodies and CD3 antibodies.

12. Hormonal Therapy

Hormonal therapy may also be used in conjunction with a glucokinase modulator of the present invention or in combination with any other secondary therapy described herein. The use of hormones may be employed to lower the level or block the effects of certain hormones that may play a role in the insulin regulation. Hormones may comprise androgens, IGF-I, and related proteins.

13. Miscellaneous Therapies

Other agents that may be contemplated in combination with a glucokinase modulator(s) of the present invention in treating diabetes include immunomodulators: linomide, ling-zhi-8, D-Glucan, multi-functional protein 14, ciamexon, cholera toxin B, vanadate, vitamin D3 analogue; lipopolysaccharide, casein hydrolysate. sulfatide, bee venom kampo formulation, silica, ganglioside, antiasialo GM-1 antibody, hyaluronidase, and concanavalin A.

14. Surgery

The present invention may also be used in conjunction with surgery. Surgery may also be used in combination with any of the other therapies used in treating diabetes or glycemic disorders as described herein.

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cell culture. βTC3 cells were cultured as described (Rizzo et al., 2002) and were transferred to media containing 1 g/L glucose overnight prior to observation. 3 h prior to experimentation, cells were washed 4 times and incubated with BMHH buffer (125 mM NaCl, 5.7 mM KCl, 2.5 mM CaCl$_2$, 1.2 mM MgCl$_2$, 10 mM Hepes, pH 7.4) containing 0.1% BSA. For FRAP, CFP-GK-YFP FRET, and nitrosylation experiments, DNA plasmids containing GK-YFP constructs, proinsulin-CFP, or CFP-GK-YFP were introduced by electroporation prior to seeding as previously described (Rizzo et al., 2002). For studies requiring co-transfection, plasmid DNA encoding the indicated constructs were transfected using either a ratio of (2 µg nNOS-CFP:1 µg GK-YFP:6 µl FUGENE (Roche Applied Science)) or of (1 µg nNOS-CFP-nuc:2 µg GK-YFP:6 µl FUGENE). Transfection was for 4 h in serum-free media, followed by replacement with low-glucose media. Observation took place the following day.

Generation of constructs. Mutations to GK-YFP were made by 4 primer PCR (with Advantage 2 Polymerase Mix, BD Biosciences Clontech) using the same set of end primers (sense 5'-GGCACCAAAATCAACGGGAC-3' (SEQ ID NO:1), antisense 5' CTCGCCCTTGCTCACCAT-3' (SEQ ID NO:2)) along with primers containing the mutation (C220S sense 5'-GACCGCCAATCTGAGGTCG-3' (SEQ ID NO:3), antisense 5'-CGACCTCAGATTGGCGGTCT-3' (SEQ ID NO:4); C364S sense 5'-CACCGACTC-CGATATCGTGC-3' (SEQ ID NO:5), antisense 5'-CAC-GATATCGGAGTCGGTGAC-3' (SEQ ID NO:6); C371S sense 5'-CCGTGCCTCTGAAAGCGTG-3' (SEQ ID NO:7), antisense 5'-CACGCTTTCAGAGGCACGGC-3' (SEQ ID NO:8); C434S sense 5'-CACCCAACTC-CGAAATCACCT-3' (SEQ ID NO:9), antisense 5'-GGT-GATTTCGGAGTTGGGTG-3' (SEQ ID NO:10)). Mutated GK was then inserted into CFP-GK-YFP using restriction sites to replace wild type GK. For bacterial expression, GK and GK(C371S) were excised from GK-YFP plasmids using BglII and XmaI and ligated into the BamHI and XmaI sites in pQE30 (Qiagen). In order to create nNOS-CFP constructs, a silent mutation was introduced into the rat cDNA for nNOS in order to remove the AgeI restriction site using the QuickChange Site-Directed Mutagenesis Kit (Stratagene) (sense primer 5'-GGGATGACAACCGATACCACGAG-GACATC-3' (SEQ ID NO: 11), antisense primer 5'-GAT-GTCCTCGTGGTATCGGTTGTCATCCC-3' (SEQ ID. NO:12)). The cDNA for the modified rat nNOS was then amplified by PCR (sense 5'-AGCTAGCCACCATGGAA-GAGAACACG-3' (SEQ ID NO:13), antisense 5'-TTAAC-CGGTGAGCTGAAAACCTCATCTGC-3' (SEQ ID NO:14)) and inserted into the NheI and AgeI restriction sites in the pECFP-nuc vector (BD Biosciences Clontech) and a derivative vector with the nuclear localization signal removed by BamHI and BglII digestion followed by religation. All primers were custom synthesized and purified by IDT. All plasmid constructs were purified using DNA preparation kits (Qiagen) and the sequences of all constructs were verified by sequencing reactions performed by the Vanderbilt-Ingram Cancer Center DNA Sequencing Shared Resource.

Microscopy. βTC3 cells were labeled with 5 µM DAF-FM diacetate (Molecular Probes) for 25 min at 25° C. in BSA free BMHH. Observation was with 488 nm excitation and 505–530 nm collection by laser scanning confocal microscopy (Zeiss LSM510). During observation, cells were heated to 32° C. using a Bioptechs Delta T system. FRAP and intramolecular FRET measurements were performed on cultured βTC3 cells as previously described (Rizzo et al., 2002). Statistical significance (p<0.05 by ANOVA or t-test as appropriate) is denoted by * and was determined from at least three granules in the same region or at least three cells for the FRET studies as compared to pre-treatment FRET ratios. Data shown is representative of at least 3 independent trials. Observation of nNOS-CFP-nuc and GK-YFP were performed using the same filter settings as the FRAP measurements. FRET between nNOS-CFP and GK-YFP was observed using 864 nm two-photon excitation along with a KP700/514 main beam splitter and standard CFP and YFP collection using a 40×, 1.3NA F-FLUAR oil immersion objective lens. For the FRET measurements, the temperature was maintained at 37° C. using a Zeiss S-M incubator controlled by the CTI temperature regulator along with humidification and an objective heater.

Detection of nitrosylated proteins. S-nitrosylated proteins were biotinylated and isolated from cell lysates using the protocol described (Jaffrey et al., 2001). Briefly, cells were lysed in HEN buffer (250 mM Hepes pH7.7, 1 mM EDTA, 0.1 mM neocuproine) using 0.5% triton X-100 and 0.5% Cholate prior to protection of free cysteines with methyl methanethiosulfonate (Pierce) and derivatization of S-nitrosylated cysteines with ascorbic acid and biotin-HPDP (Pierce). Biotinylated proteins were either isolated by binding to neutravidin-agarose (Pierce), followed by 5 washes with a high salt buffer (20 mM Hepes pH 7.7, 600 mM NaCl, 1 mM EDTA and 0.5% Triton X-100) and elution in HNE buffer (20 mM Hepes pH 7.7, 100 mM NaCl, 1 mM EDTA) plus 100 mM 2-mercaptoethanol. Alternatively, GK-YFPs were isolated by immunopreciptation with A.V. Peptide Antibody (BD BioSciences Clontech) preconjugated to IgG agarose (Sigma). Western blots were then performed on eluted proteins to detect GK and nitrosylated proteins.

Kinetic analysis of GK mutations. His-tagged recombinant GK and GK(C371S) were produced in M15(pREP4) cells and purified by Ni:NTA affinity chromatography (Qiagen) precisely as described (Tiedge et al. 1997). Protein concentrations were determined using the Advanced Protein Assay (Cytoskeleton Inc.) at $A_{590}$ according to the manufacturer's protocol. Kinetic analysis was performed on 2 mUnits of purified protein at 37° C. using a photometric assay containing 50 mM Hepes (pH 7.2), 100 mM KCl, 10 mM $MgCl_2$, 2.5 mM dithiothreitol, 5 mM ATP, 2 mM NAD+, 4 Units/ml glucose-6-phosphate dehydrogenase from Leuconostoc mesenteroides, and varying concentrations of glucose. One unit was defined as the amount of protein required to produce 1 μmole NADH per minute. NADH production was assayed from stopped reactions (1 ml cold 500 mM $NaHCO_3$ per 100 μl reaction mix) as previously described (Rizzo et al., 2002), and reaction velocities were calculated from reaction time courses over 2 min as a function of glucose concentration. $K_m$ and $V_{max}$ were calculated from linear regression analysis of Hanes-Woolf plots using Prism software (Graphpad, San Diego, Calif.).

Immunoprecipitation. BMHH starved cells from one 60 mm dish were collected in cold phosphate buffered saline, pH 7.4 (PBS, prepared from. 10× solution (Gibco) and resuspended in lysis buffer (HNE buffer with 1% cholate, 1% triton X-100, 1× Protease Inhibitor Cocktail for use with Mammalian Cells and Tissue Extracts (Sigma)) for 20 min. Following removal of insoluble material by centrifugation (5 min, 3000×g), normalized amounts of protein (determined by Advanced Protein Assay; $A_{590}$) were incubated for 1 h with primary antibodies for GK (Jetton and Magnuson, 1992) or GFP preconjugated to 25 μl agarose IgG in 750 μl lysis buffer. Precipitates were washed twice in lysis buffer and three times in HNE buffer prior to analysis by Western blot or treatment with DEANO (Molecular Probes).

Example 2

Results and Discussion

To assess the role of NOS in the regulation of GK by insulin, the inventors examined whether insulin could stimulate NO production in β cells. βTC3 cells were loaded with 4-amino-5-methylamino-2',7'-difluorofluorescein diacetate (DAF-FM) (Kojima et al., 1999), an indicator dye whose fluorescence increases upon reaction with NO. A rapid increase in the fluorescence of DAF-FM was observed within minutes in insulin-treated cells as compared to untreated cells (FIG. 1A). This indicates that insulin treatment results in NO production on a time-scale consistent with regulation of GK (Rizzo et al., 2002). The inventors also examined the role of NOS activation in the regulation of GK association with secretory granules. Association of GK with secretory granules was analyzed in cells expressing a YFP labeled GK (GK-YFP) and a CFP targeted to insulin granules by insertion into a proinsulin cDNA (Watkins et al., 2002; Rizzo et al., 2002) (FIG. 1B). Association of GK-YFP with CFP-labeled granules can be assayed by selectively photobleaching the GK-YFP in a small region of the cell (white box, FIG. 1B) and monitoring the FRAP to the CFP-labeled granules. Recovery of GK-YFP to CFP-labeled granules occurs at a faster rate in insulin treated cells (FIG. 1C), which indicated a net translocation of GK to the cytoplasm (Rizzo et al., 2002). A significant difference in the degree of fluorescence recovery between insulin treated (5 min, 100 nM) and untreated cells could be reliably measured 2 s into recovery (FIG. 1D). Inhibition of NOS activity using $N^G$-nitro-L-arginine-methyl ester (L-NAME) blocked the stimulatory effects of insulin on GK-YFP FRAP, indicating a requirement for NO production. Furthermore, the effects of NOS inhibition were reversed by treatment with S-nitroso-N-acetylpenicillamin (SNAP), an NO releasing agent.

The requirement for NO production in GK regulation was also tested using a fluorescence resonance energy transfer (FRET)-based assay to examine changes in GK conformation. The FRET ratio between CFP and YFP inserted on opposing ends of GK decreases in cells treated with insulin (FIG. 1E), and correlated with increased GK activity (Rizzo et al., 2002). Treatment with L-NAME prevented the decrease in the FRET ratio observed with insulin treatment alone. A decrease in the FRET ratio was observed in cells treated with an NO releasing agent either in the presence of L-NAME and insulin, or in the absence of other treatments. These results suggest that NO production is a regulator of GK and mediates the effects of insulin treatment. Glucose stimulated activation of GK FRAP and FRET was also sensitive to treatment with L-NAME (data not shown), and is consistent with the effect of glucose stimulated insulin secretion on auto feedback regulation of GK (Rizzo et al., 2002).

To determine whether regulation of GK by NO is the result of direct post-translational modification of GK, the inventors examined whether GK was S-nitrosylated in insulin treated cells. Nitrosylated proteins from cell lysates were chemically modified with biotin (Jaffrey et al., 2001) prior to isolation using neutravidin-agarose and analysis by Western blot. Nitrosylated GK was detected only in precipitates from insulin treated cells, but not from untreated cells or cells treated with L-NAME in addition to insulin. These results along with the fluorescence-based assays, support a model in which changes in GK localization and activity are related to S-nitrosylation of GK.

Figure 2A:
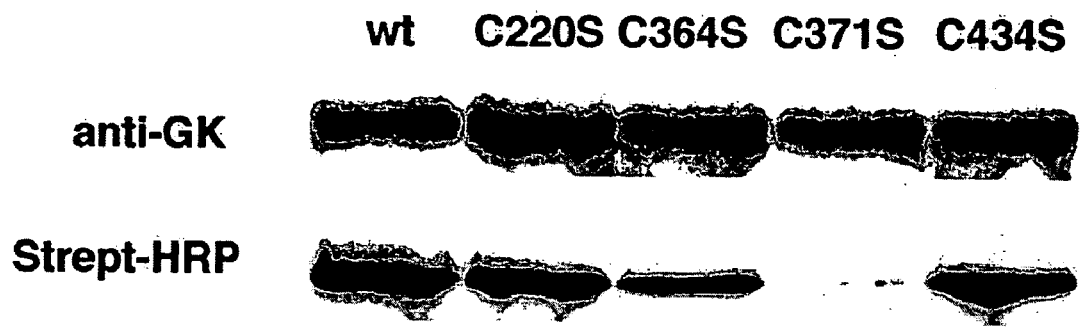
FIGS. 2A–2C. Nitrosylation of cysteine 371 is required for GK regulation.
Figure 2B:
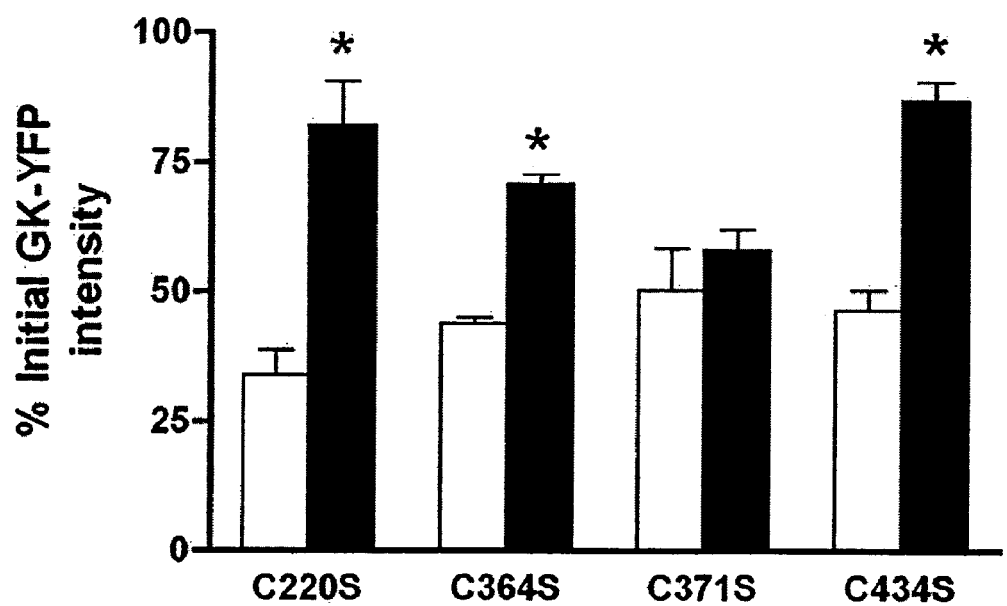
Figure 2C:
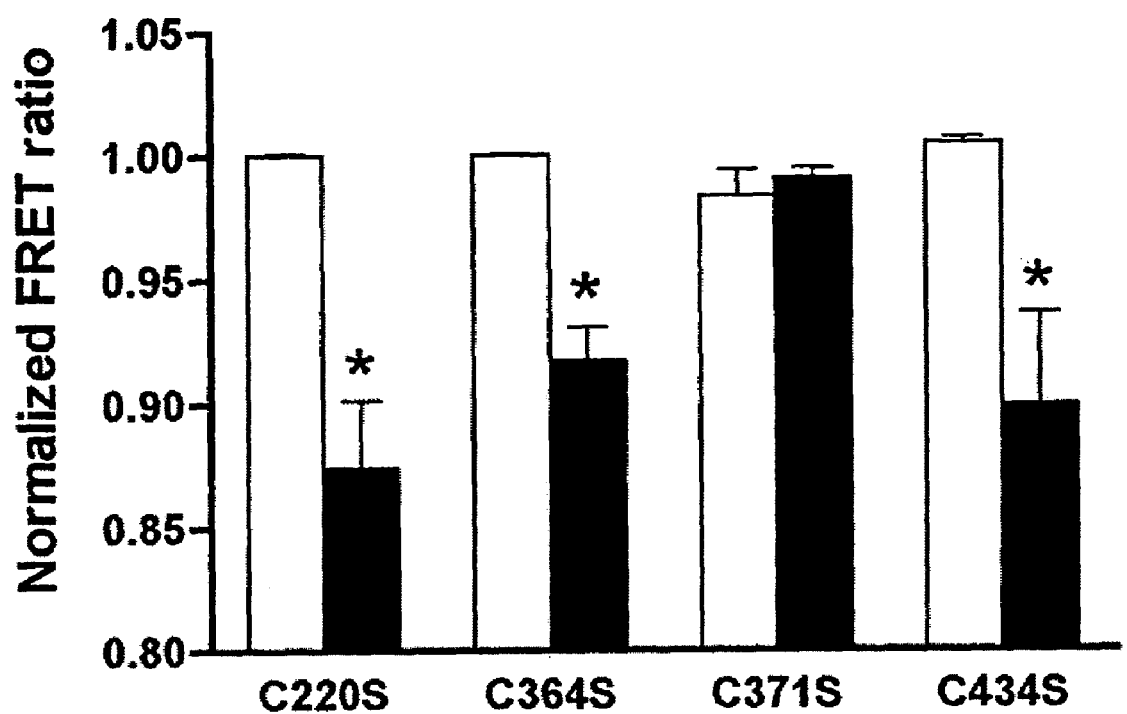

To test the role of S-nitrosylation in regulating GK, the inventors examined whether site directed mutagenesis of GK could block its nitrosylation and affect its regulation. Since reaction of NO with cysteines can be greatly enhanced by a consensus nitrosylation motif (Stamler et al., 1997), the inventors examined the primary structure of GK for potential nitrosylation sites. Four such consensus sites were found in GK (C220, C364, C371, and C434) and each was subsequently mutated to serine, an amino acid that does not react with NO. The mutant GK constructs were tagged with YFP, and the S-nitrosylation of the mutated proteins was assessed (FIG. 2A). Of the four mutations generated, only C371S eliminated GK nitrosylation, although a slight decrease in the amount of nitrosylated GK was observed for the C364S mutation. Furthermore, the C371S mutant stopped insulin-stimulated FRAP to CFP labeled granules (FIG. 2B), and changes in FRET (FIG. 2C). Mutation of C364S did not have a significant effect on insulin-stimulated FRAP to CFP labeled granules (FIG. 2B) and changes in FRET (FIG. 2C). The, nitrosylation of cysteine 371 played a key role in modulating GK association with secretory granules and conformational changes that correlate with GK activation.

To assess the role of C371 in regulating GK activity, the kinetic parameters of recombinantly expressed and purified GK(C371S) were examined and compared with the kinetic parameters of native GK. GK-C371S was found to have an increased $K_m$ for glucose (12.5±2.5 mM) and a reduced $V_{max}$ (30.6±0.3 U/mg protein) as compared to GK ($K_m$=8.7±1.3 mM; $V_{max}$=48.1±2.7 U/mg protein). Because of the reducing agents needed to stabilize recombinantly expressed GK (Tippett and Neet, 1983; Tiedge et al., 1997; Matschinsky et al., 1998), the effect of S-nitrosylation on GK activity in vitro could not be determined. However, analysis of GK(C371S) was consistent with a previous analysis (Tiedge et al., 2000) and shows that modification of C371 alters the enzymatic activity of GK.

Figure 3A:
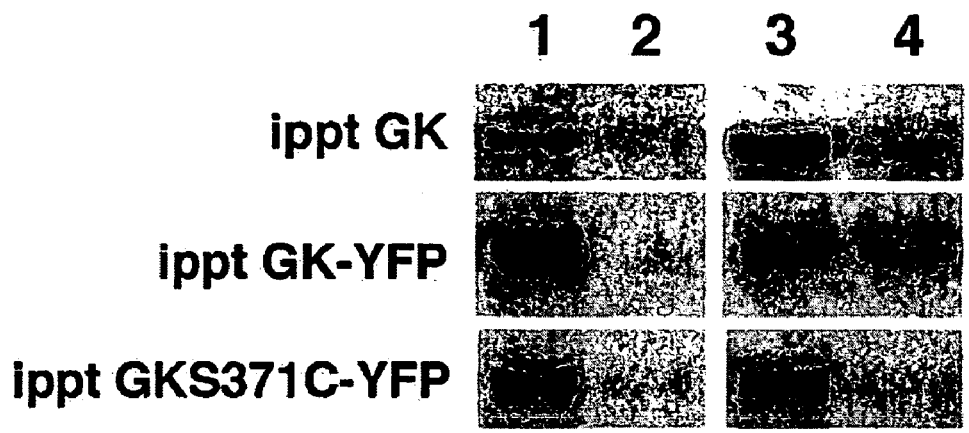
FIGS. 3A–3D. Association of GK with nNOS can direct GK localization.

Since other proteins that react with NO are known to form complexes containing nNOS (Brenman et al., 1996; Fang et al., 2000; Nedvetsky et al., 2002), the inventors examined the role of nNOS in determining GK localization. To detect interaction between GK and nNOS, the inventors immunoprecipitated endogenous GK from cell lysates and probed for endogenous nNOS by Western blot (FIG. 3A). The inventors were able to detect nNOS in these precipitates and also from those of expressed GK-YFP and GK(C371S)-YFP. Incubation of GK precipitates with diethylamine nitric oxide (DEANO), a chemical that rapidly releases NO, resulted in elution of nNOS from endogenous GK and GK-YFP precipitates, but not from GK(C371S)-YFP precipitates. Thus, GK association with nNOS was both consistent with GK association with secretory granules and also sensitive to the presence of NO.

Figure 3B:
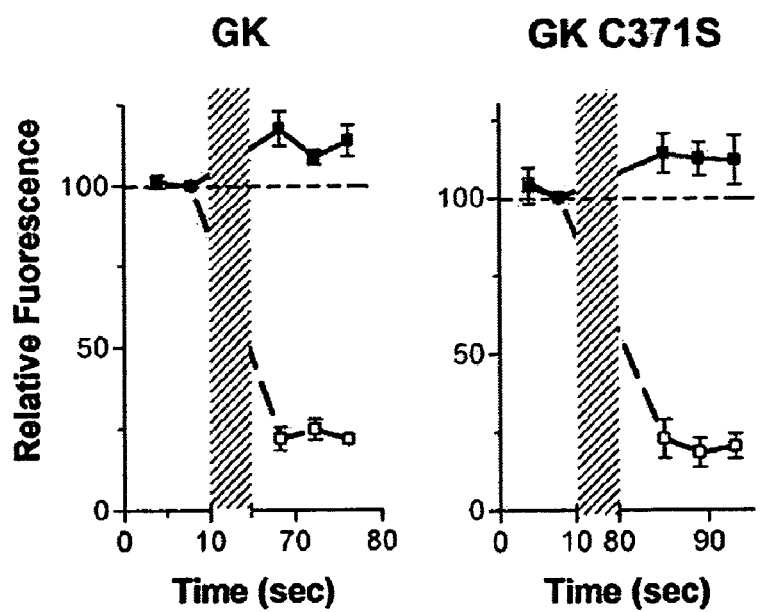
Figure 3C:
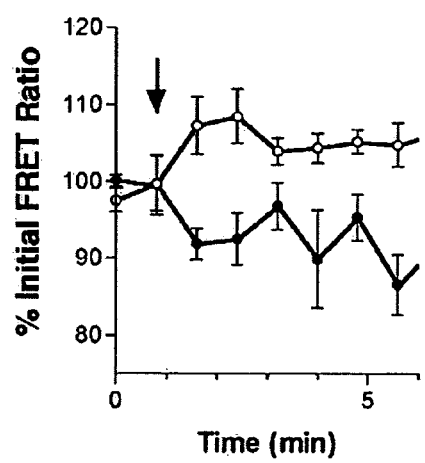
Figure 3D:
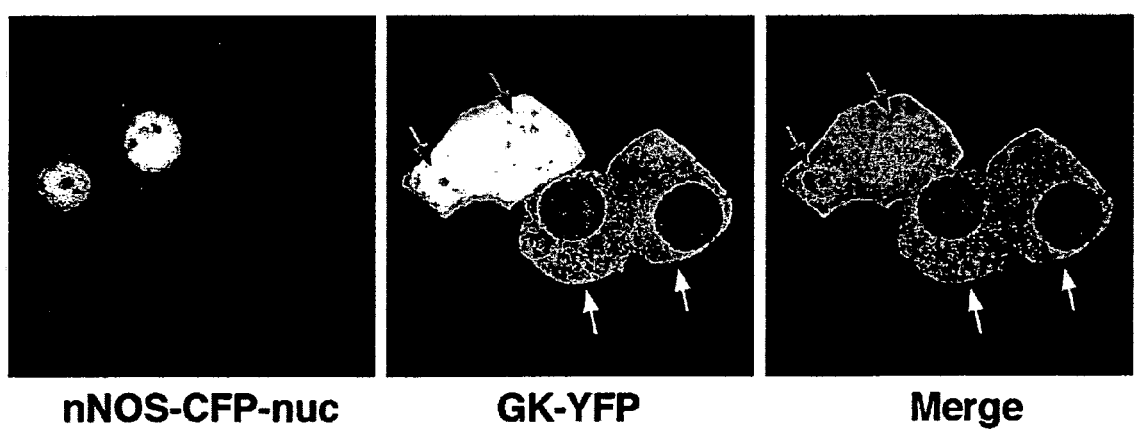

Interaction between nNOS and GK was also examined in living cells by measuring changes in FRET between CFP labeled nNOS and GK-YFP. FRET between nNOS-CFP and GK-YFP was verified by acceptor photobleaching of either GK-YFP or GK(C371S)-YFP, which caused an increase in nNOS-CFP fluorescence (FIG. 3B). Insulin treatment resulted in a decrease of the FRET between nNOS-CFP and GK-YFP, while FRET between nNOS-CFP and GK(C371S)-YFP increased (FIG. 3C). The increase in FRET between nNOS-CFP and nitrosylation resistant GK(C371S)-YFP was most likely due to dissociation of competing endogenous GK and association of unbound GK(C371S)-YFP to the vacated NOS binding sites. These results indicated that GK and nNOS interact on secretory granules either directly or as part of a complex. To determine whether the interaction between GK and nNOS was sufficient to determine GK localization, the inventors targeted nNOS-CFP to the nucleus. A nuclear localization sequence from simian virus 40 large T-antigen (Kalderon et al., 1984; Lanford et al., 1986) was attached to the C-terminus of nNOS-CFP and co-expressed in β cells with GK-YFP. GK-YFP localized to the nuclei of cells only when co-expressed with the nucleus-targeted nNOS-CFP (FIG. 3D). Since the subcellular localization of GK can be determined by the localization of nNOS, it suggests that nNOS may be the primary target for GK on secretory granules.

Overall, the data indicated that the GK localization and activity in the β cell are determined by GK association with nNOS and that association is disrupted by GK nitrosylation at cysteine 371. Regulation of GK-NOS association by nitrosylation provided a sensitive means for modulating GK activity, thus affecting glucose-stimulated insulin secretion. In addition, the data demonstrated that changes in protein nitrosylation can regulate protein localization, protein-protein interactions, and protein function in a highly specific and rapid way that is similar to the role of protein phosphorylation.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

Adams et al., *Biochim. Biophys. Acta*, 932:195–205, 1988.
Ashcroft et al., *Biochem. J.*, 126:525–532, 1972.
Ashcroft et al., *Biochem. J.*, 132:223–231, 1973.
Aspinwall et al., *J Biol. Chem.*, 275:22331–22338, 2000.
Bajorin et al., *J Clin. Oncol.*, 6(5):786–92, 1988.
Bell et al., *Annu. Rev. Physiol.*, 58:171–186, 1996.
Bell et al., *Proc. Natl. Acad. Sci. USA*, 88:1484–1488, 1991.
Brenman et al., *Cell*, 84:757–767, 1996.
Cambridge, *Br. Med. J.*, 2:738–741, 1928.
Culver et al., *Science*, 256(5063):1550–1552, 1992.
Dukes et al, *J. Biol. Chem.*, 269:10979–10982, 1994.
Dukes et al., *J. Biol. Chem.*, 269:10979–10982, 1994.
Efrat et al., *Proc. Natl. Acad. Sci. USA*, 91:2051–2055, 1994.
Erecinska et al., *Biochim. Biophys. Acta*, 1101:271–295, 1992.
Fajans, *Diabetes/Metab. Rev.*, 5:579–606, 1989.
Fang et al., *Neuron*, 28:183–193, 2000.
Froguel et al., *N. Engl. J. Med.*, 328:697–702, 1993.
Froguel et al., *Nature (London)*, 356:162–164, 1992.
Gerbitz et al., *Diabetes*, 45:113–126, 1996.
Grupe et al., *Cell*, 83:69–78, 1995.

Harlow and Lane, Antibodies: A Laboratory manual, Cold Spring Harbor Laboratory, 1988.
Hattersley et al., *Lancet.*, 339:1307–1310, 1992.
Heimberg et al., *EMBO J.*, 12:2873–2879, 1993.
Henningsson et al., *Am. J Physiol. Cell. Physiol.*, 283: C296–C304, 2002.
Iynedjian, *Biochem. J.*, 293:1–13, 1993.
Jaffrey et al., *Nat. Cell Biol.*, 3:193–197, 2001.
Jetton and Magnuson, *Proc. Natl. Acad. Sci. USA*, 89:2619–2623, 1992.
Kalderon et al., *Cell*, 39:499–509, 1984.
Kaneko et al., *Am. J. Physiol. Cell. Physiol.*, 10:1152, 2003.
Kerr et al., *Br. J. Cancer*, 26(4):239–257, 1972.
Kojima et al., *Angew. Chem. Int. Ed. Engl.*, 38:3209–3212, 1999.
Lajoix et al., *Diabetes* 50:1311–1323, 2001.
Lanford et al., *Cell*, 46:575–582, 1986.
Laterveer et al., In: *Modern Trends in Biothermokinetics* 3, Gnaiger et al. Eds.), NY, Plenum, 186–190, 1994.
Leibiger et al., *Mol. Cell*, 7:559–570, 2001.
Longo et al., *J. Biol. Chem.*, 266:9314–9319, 1991.
MacDonald and Fahien, *Arch. Biochem. Biophys.*, 279: 104–108, 1990.
Magnuson and Shelton, *J. Biol. Chem.*, 264:15936–15942, 1989.
Magnuson et al., *Proc. Natl. Acad. Sci. USA*, 86(13):4838–4842, 1989.
Magnuson et al., *Proc. Natl. Acad. Sci. USA*, 86:4838–4842, 1989.
Magnuson, *Diabetes*, 39:523–527, 1990.
Malaisse, *Int. J. Biochem.*, 5:593–701, 1992.
Malaisse-Lagae and Malaisse, *Biochem. Med. Metab. Biol.*, 39:80–89, 1988.
Matschinsky et al., *Diabetes*, 47:307–315, 1998.
Matschinsky, *Diabetes*, 39:647–652, 1990.
Matschinsky, *Diabetes*, 45:223–241, 1996.
Matschinsky, *Diabetes*, 51 :S394–404, 2002.
Meglasson and Matschinsky, *Diabetes Metab. Rev.*, 2:163–214, 1986.
Mitchell et al., *Ann. NY Acad. Sci.*, 690:153–166, 1993.
Mitchell et al., *J. Clin. Oncol.*, 8(5):856–869, 1990.
Muller et al., *Arch. Biochem. Biophys.*, 308:8–23, 1994.
Nedvetsky et al., *Proc. Natl. Acad. Sci. USA*, 99:16510–16512, 2002.
Newgard and McGarry, *Annu. Rev. Biochem.*, 64:689–719, 1995.
O'Rahilly et al., *Diabetologia*, 31:407–414, 1988.
Orci, *Diabetes*, 31:538–565, 1982.
PCT Appl. WO 84/03564
Pilkis and Granner, *Annu. Rev. Physiol.*, 54:885–909, 1992.
Rasschaert and Malaisse, *Biochim. Biophys. Acta*, 11015: 353–360, 1990.
Ravindranath and Morton, *Intern. Rev. Immunol.*, 7: 303–329, 1991.
Remington's Pharmaceutical Sciences, 18th Ed. Mack Printing Company, 1289–1329, 1990.
Rizzo et al., *J. Biol. Chem.*, 277:34168–34175, 2002.
Rotter et al., In: *Diabetes Mellitus: Theory and Practice*, Rifkin and Porte (Eds.), NY, 378–413, 1990.
Salehi et al., *Am. J. Physiol.*, 270:C1634–C1641, 1996.
Sener et al., *Arch. Biochem. Biophys.*, 251:61–67, 1986.
Smukler et al., *Diabetes*, 51:3450–3460, 2002.
Stamler et al., *Neuron*, 18:691–696, 1997.
Stubbs et al., *Diabetes*, 49:2048–2055, 2000.
Sweet et al., *Am. J. Physiol.*, 271:E606–E625, 1996.
Tiedge et al., *Arch. Biochem. Biophys.*, 375:251–260, 2000.
Tiedge et al., *Biochem. Biophys. Acta*, 1337:175–190, 1997.
Tippett and Neet, *Arch. Biochem. Biophys.*, 222:285–298, 1983.
Toyoda, et al., *Histochem. Cell. Biol.*, 112:35–40, 1999.
Wang and Iynedjian, *Proc. Natl. Acad. Sci. USA*, 94:4372–4377, 1997.
Watkins et al., *Traffic*, 3:461–471, 2002.
Weiler et al., *Biochem. Med.*, 33:223–235, 1985.

What is claimed is:

1. A method of screening a candidate substance for modulation of glucokinase (GK) comprising:
   (a) providing an insulin-responsive cell expressing a GK molecule;
   (b) contacting said cell with said candidate substance; and
   (c) measuring translocation of said GK molecule into the cytoplasm of said cell, wherein a change in the translocation of said GK molecule into the cytoplasm of said cell, as compared to that seen in a similar cell not treated with said candidate substance, indicates that said candidate substance is a modulator of said GK molecule.

2. The method of claim 1, wherein said insulin-responsive cell is an immortalized pancreatic cell.

3. The method of claim 1, wherein said insulin-responsive cell is an insulinoma cell.

4. The method of claim 1, wherein said insulin-responsive cell is treated with insulin, NO or high glucose concentrations.

5. The method of claim 1, wherein said insulin-responsive cell is subjected to low glucose concentrations.

6. The method of claim 1, wherein measuring comprises fluorescence photobleaching.

7. The method of claim 6, wherein said GK molecule is labeled with yellow fluorescent protein, and secretory granules are labeled with cyan fluorescent protein.

8. The method of claim 4, further comprising performing a control reaction using an inhibitor of nitric oxide synthase.

9. The method of claim 1, wherein said candidate substance is a peptide or protein.

10. The method of claim 1, wherein said candidate substance is a nucleic acid.

11. The method of claim 1, wherein said candidate substance is an activator of said GK molecule.

12. The method of claim 1, wherein said candidate substance is an inhibitor of said GK molecule.

* * * * *

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic Primer

<400> SEQUENCE: 1
ggcaccaaaa tcaacgggac        20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic Primer

<400> SEQUENCE: 2
ctcgcccttg ctcaccat        18

<210> SEQ ID NO 3

```
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
gaccgccaat ctgaggtcg                                                  19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
cgacctcaga ttggcggtct                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
caccgactcc gatatcgtgc                                                 20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
cacgatatcg gagtcggtga c                                               21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
ccgtgcctct gaaagcgtg                                                  19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
cacgctttca gaggcacggc                                                 20

<210> SEQ ID NO 9
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
cacccaactc cgaaatcacc t                                             21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
ggtgatttcg gagttgggtg                                               20

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
gggatgacaa ccgataccac gaggacatc                                     29

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
gatgtcctcg tggtatcggt tgtcatccc                                     29

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
agctagccac catggaagag aacacg                                        26

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
ttaaccggtg agctgaaaac ctcatctgc                                     29
```